US010202976B2

(12) United States Patent
Bielefeldt et al.

(10) Patent No.: US 10,202,976 B2
(45) Date of Patent: Feb. 12, 2019

(54) SYSTEM AND METHOD FOR EMISSIONS TESTING A COMPRESSOR, TURBINE, OR ENGINE

(71) Applicant: NEARSHORE NATURAL GAS, LLC, Houston, TX (US)

(72) Inventors: Daniel P. Bielefeldt, Lincoln University, PA (US); Aaron J. Hilber, Houston, TX (US)

(73) Assignee: Nearshore Natural Gas, LLC, Houston, TX (US)

( * ) Notice: Subject to any disclaimer, the term of this patent is extended or adjusted under 35 U.S.C. 154(b) by 169 days.

(21) Appl. No.: 15/440,041

(22) Filed: Feb. 23, 2017

(65) Prior Publication Data

US 2017/0248137 A1 Aug. 31, 2017

Related U.S. Application Data

(60) Provisional application No. 62/300,023, filed on Feb. 25, 2016.

(51) Int. Cl.
*F04B 51/00* (2006.01)
*F04B 35/00* (2006.01)
(Continued)

(52) U.S. Cl.
CPC ............ *F04B 51/00* (2013.01); *F04B 35/002* (2013.01); *F04D 27/001* (2013.01); *F17C 7/00* (2013.01);
(Continued)

(58) Field of Classification Search
CPC .... F04B 51/00; F04B 35/002; F04B 2203/06; G01N 33/004; F04D 27/001; G01M 15/102; F17C 7/00; F17C 13/026; F17C 13/025; F17C 2250/03; F17C 2227/04; F17C 2227/0157; F17C 2221/033; F17C 2250/0626

See application file for complete search history.

(56) References Cited

U.S. PATENT DOCUMENTS 4,784,399 A * 11/1988 Finn .......................... B60P 7/12
280/837
5,810,058 A * 9/1998 Kountz ...................... F17C 5/06
141/18

(Continued)

FOREIGN PATENT DOCUMENTS

WO    WO 2014/031999 A2    2/2014

OTHER PUBLICATIONS

U.S. Appl. No. 62/279,388, filed Jan. 15, 2016, titled "Compressed Natural Gas Artificial Gas Lift".

*Primary Examiner* — Freddie Kirkland, III
(74) *Attorney, Agent, or Firm* — Pillsbury Winthrop Shaw Pittman LLP

(57) ABSTRACT

A mobile compressed natural gas (CNG) vessel and unloader are used to supply CNG to a compressor during regulatory emissions testing of the compressor (e.g., U.S. EPA's Quad J testing). CNG output by the compressor is recirculated to an inlet of the unloader so that it is reused during the emissions testing. Lean CNG from the vessel may be used to power the compressor during the testing. The unloader ensures that the compressor is run at at least a predetermined load factor during the emissions testing.

18 Claims, 4 Drawing Sheets

(51) Int. Cl.
  *F04D 27/00* (2006.01)
  *G01N 33/00* (2006.01)
  *G01M 15/10* (2006.01)
  *F17C 7/00* (2006.01)
  *F17C 13/02* (2006.01)

(52) U.S. Cl.
  CPC .......... *F17C 13/025* (2013.01); *F17C 13/026* (2013.01); *G01M 15/102* (2013.01); *G01N 33/004* (2013.01); F04B 2203/06 (2013.01); F17C 2221/033 (2013.01); F17C 2227/0157 (2013.01); F17C 2227/04 (2013.01); F17C 2250/01 (2013.01); F17C 2250/03 (2013.01); F17C 2250/0626 (2013.01); F17C 2250/0631 (2013.01); F17C 2260/044 (2013.01); F17C 2270/01 (2013.01)

(56) References Cited

U.S. PATENT DOCUMENTS

| | | | | |
|---|---|---|---|---|
| 6,429,019 | B1* | 8/2002 | Goldstein | G01N 33/004 436/134 |
| 7,059,364 | B2* | 6/2006 | Kountz | F17C 9/02 141/197 |
| 7,178,565 | B2* | 2/2007 | Eichelberger | B60S 5/02 141/39 |
| 7,186,094 | B2* | 3/2007 | Edlund | F04B 49/00 417/63 |
| 8,122,918 | B2* | 2/2012 | Handa | F17C 5/00 141/192 |
| 9,863,581 | B2* | 1/2018 | Santos | F17C 5/06 |
| 9,951,905 | B2* | 4/2018 | Barker | F17C 5/06 |
| 10,077,871 | B2* | 9/2018 | Blanchet | F17C 5/06 |
| 2015/0211684 | A1* | 7/2015 | Santos | F17C 5/06 137/1 |

* cited by examiner

SYSTEM AND METHOD FOR EMISSIONS TESTING A COMPRESSOR, TURBINE, OR ENGINE

CROSS REFERENCE

This application claims the benefit of priority from U.S. Provisional Application No. 62/300,023, filed Feb. 25, 2016, titled "System And Method For Emissions Testing A Compressor," the entire contents of which are hereby incorporated by reference herein.

BACKGROUND

1. Field of the Invention

Various embodiments relate generally to emissions testing of compressors.

2. Description of Related Art

Regulatory requirements in various jurisdictions require that certain compressors (e.g., compressors with a horsepower size over a certain value) must be periodically emissions tested to verify that their emissions are within acceptable limits. The U.S. Environmental Protection Agency's JJJJ ("Quad J") regulations create such requirements in the United States. Other jurisdictions (e.g., countries, states) have similar regulations.

In the U.S., if a compressor is tested at 90% or more of its rated load, the EPA recognizes that emissions in other applications will not be significantly more than during the test and as such reduces the testing frequency requirements. The rules state that a compressor must be tested annually and after each move/relocation if the load factor during the test is less than 90% of the compressor's rated load. If the load factor is 90% or more of the compressors rated load, then the compressor must be tested every three years and after each move/relocation. In addition, a test at 90% load has a wider tolerance window for emissions results.

SUMMARY

Compressors in their typical environments may not have the available infrastructure, supply of gas, or consumer of gas, to facilitate a test at ≥90% load (which requires a combination of pressure and flow rate). Also the composition of the available process gas might cause higher emissions than would happen with more standard lean natural gas composed of mostly methane. In such circumstances, it was common to just perform the emissions testing at below 90% load with whatever gas was available. In some instances, an end user might connect a pipeline for the compressor fuel gas for cleaner/leaner emissions. This requires additional infrastructure in piping, metering, etc., as well as additional accounting and operational complexities to purchase such gas.

Conventional compressor testing when there was insufficient gas supply or downstream consumption for the test to be run at ≥90% load results in end users needing to test the compressors more frequently than otherwise required. Also, tests are often failed and need to be repeated because of a small tolerance band resulting from the lower load factor, combined with higher emissions resulting from gas composition. The higher frequency and repeat tests have significant cost consequences.

One or more embodiments address this issue by providing an apparatus and method that provide sufficient supply and consumption of gas to facilitate optimal pressure and/or flowrate conditions (e.g., ≥90% load conditions) by providing: (1) a mobile natural gas vessel that provides sufficient gas supply for the regulatory testing of the compressor, and (2) an unloader that receives compressed gas from the compressor, conditions it (e.g., by reducing its pressure), and recirculates it to the compressor to ensure that the downstream gas is consumed at a sufficient rate (e.g., via recirculation) to continue running the compressor at a desired load (e.g., ≥90% of the compressor's rated load). The mobile natural gas vessel may act as (1) source of CNG during the emissions testing, and (2) a buffer/expansion tank to receive excess compressed gas from the compressor.

One or more non-limiting embodiments provide a method for testing a compressor. The method includes: transferring compressed gas from a storage vessel of a mobile compressed gas storage system to an inlet of a compressed gas unloader and recirculating at least a portion of the compressed gas received by the unloader between the unloader and a compressor. The recirculating includes: reducing, via the unloader, a pressure of compressed gas received at the inlet of the unloader, transferring the reduced pressure gas from the unloader to an inlet of the compressor, recompressing, via the compressor, the reduced pressure gas received from the unloader, and transferring at least a portion of the recompressed gas back to the inlet of the unloader. The method also includes, during the recompressing, conducting emissions testing (e.g., Quad J testing, other regulatory emissions testing) on the compressor.

According to one or more embodiments, the compressor includes a gas-powered engine for driving a compressor portion of the compressor, and conducting emissions testing on the compressor includes conducting emissions testing on the engine.

According to one or more of these embodiments, the compressed gas comprises a compressed fuel gas (e.g., natural gas, propane, etc.). According to one or more of these embodiments, the compressor comprises an engine-driven compressor that includes an internal combustion engine.

One or more of these methods also includes, during the recirculating, powering the engine of the compressor with the compressed fuel gas received from the compressed gas storage vessel.

According to one or more of these embodiments, the emissions testing comprises regulatory emissions testing that is required by a regulatory authority for the compressor (e.g., U.S. EPA Quad J testing).

According to one or more of these embodiments, during the recirculating, the compressed gas storage vessel acts as a buffer vessel to accept excess compressed gas from the compressor.

According to one or more of these embodiments, during the recirculating, the compressed gas storage vessel provide makeup compressed gas to unloader.

One or more of these methods also includes, during the recirculating, transferring sufficient compressed gas from the compressed gas storage vessel to the compressed gas unloader that the recompressing occurs at at least a predetermined portion of a rating of the compressor (e.g., 80%, 90%, 95% of the compressor's rating).

According to one or more of these embodiments, the compressor is one of: a pipeline booster station compressor, a vapor recovery compressor of a well, and a gas lift compressor of a gas lift well.

One or more of these methods also includes, before the recirculating, transporting the compressed gas storage vessel and the unloader to a geographical site where the compressor is located.

According to one or more of these embodiments, during the recirculating, the unloader controls a pressure of the reduced pressure gas being transferred to the inlet of the compressor so that the pressure of the reduced pressure gas at the inlet of the compressor remains within a predetermined pressure range.

According to one or more of these embodiments, during the recirculating, the unloader controls a temperature of the reduced pressure gas being transferred to the inlet of the compressor so that the temperature of the reduced pressure gas at the inlet of the compressor remains within a predetermined temperature range.

According to one or more of these embodiments, during the recirculating, the unloader controls a pressure of the gas being received by the unloader's inlet from the compressor's outlet so that an outlet pressure of the compressor remains above a predetermined value.

One or more of these methods also includes: before conducting the emissions testing, disconnecting the compressor from a downstream gas line that the compressor's outlet feeds during the compressor's routine operation; and after conducting the emissions testing, reconnecting the compressor to the downstream gas line.

One or more of these methods also includes: before conducting the emissions testing, disconnecting the compressor from an upstream gas supply line that feeds the compressor during the compressor's routine operation; and after conducting the emissions testing, reconnecting the compressor to the upstream gas supply line.

One or more embodiments provides a system for emissions testing a compressor. The system includes: the compressor, the compressor having an inlet and an outlet; a mobile compressed gas storage system including a compressed gas vessel supported by a wheeled frame, the compressed gas vessel containing compressed gas at a supply pressure; and an unloader having an inlet and an outlet, the inlet of the unloader being fluidly connected to the vessel and the outlet of the compressor, the outlet of the unloader being fluidly connected to the inlet of the compressor. The system is configured to recirculate compressed gas through the unloader and compressor during emissions testing of the compressor. According to various embodiments, the system also includes any one or more of the features of the above-described methods.

One or more of these and/or other aspects of various embodiments, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment, the structural components illustrated herein are drawn to scale. It is to be expressly understood, however, that the drawings are for the purpose of illustration and description only and are not intended as a definition of the limits of the invention. In addition, it should be appreciated that structural features shown or described in any one embodiment herein can be used in other embodiments as well. As used in the specification and in the claims, the singular form of "a", "an", and "the" include plural referents unless the context clearly dictates otherwise.

All closed-ended (e.g., between A and B) and open-ended (greater than C) ranges of values disclosed herein explicitly include all ranges that fall within or nest within such ranges. For example, a disclosed range of 1-10 is understood as also disclosing, among other ranged, 2-10, 1-9, 3-9,etc.

Unless otherwise stated, the term "about," with reference to a number, means within 5% of that number.

BRIEF DESCRIPTION OF THE DRAWINGS

For a better understanding of various embodiments as well as other objects and further features thereof, reference is made to the following description which is to be used in conjunction with the accompanying drawings, where.

DETAILED DESCRIPTION OF EXEMPLARY EMBODIMENTS

Compressor Test System 10

Figure 1:
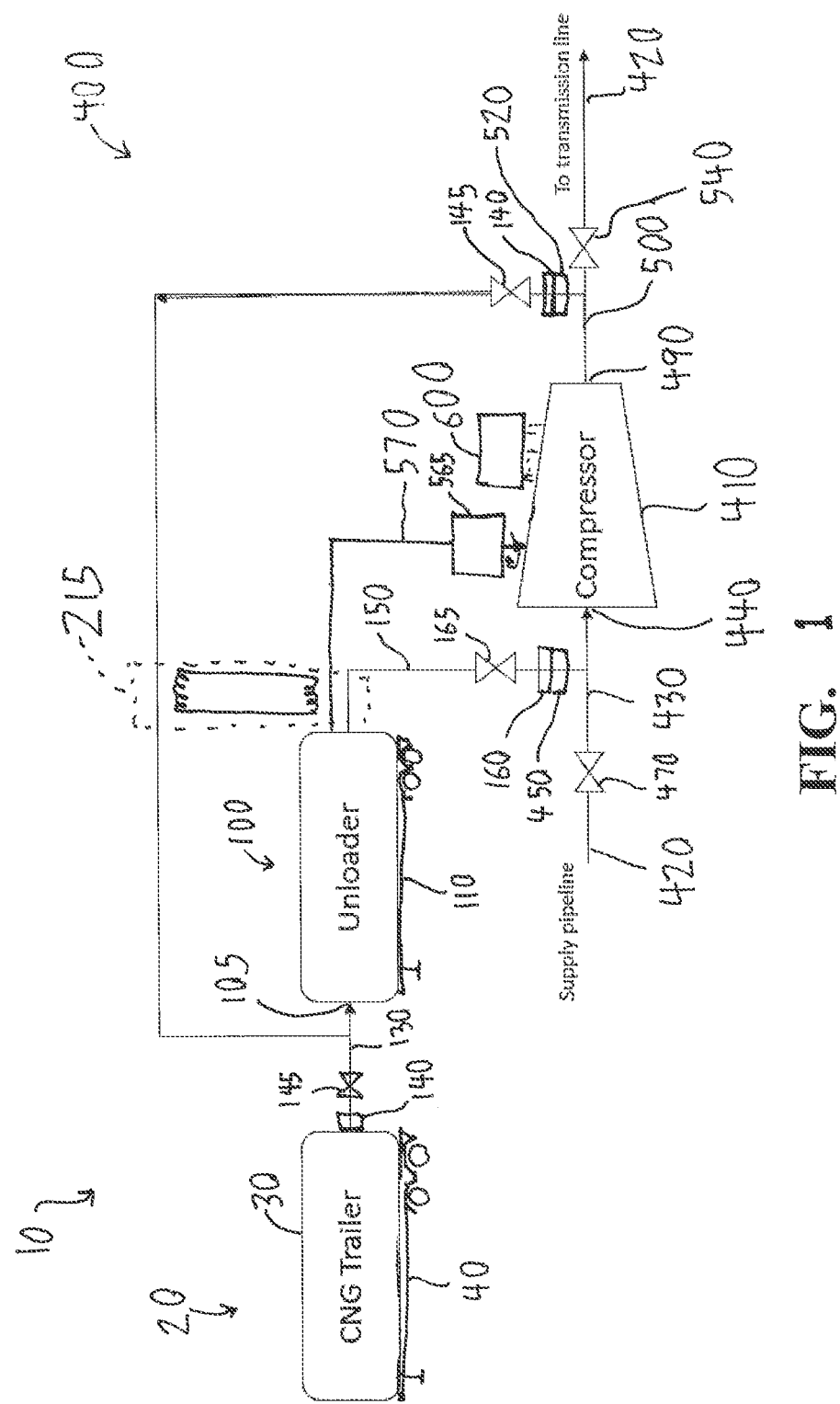
FIG. 1 is a diagrammatic view of a compressor test system being used with a compressor of a compressed natural gas (CNG) transmission pipeline.

As shown in FIG. 1, one ore more embodiments provide a compressor test system 10 for emissions testing a compressor 410. The test system 10 comprises a compressed natural gas (CNG) mobile storage system 20 and a compressed gas unloader 100.

CNG Mobile Storage System 20

As shown in FIG. 1, the CNG mobile storage system 20 comprises a CNG vessel 30 supported by a mobile frame 40. The vessel 30 may be removably or permanently mounted to the mobile frame 40. In the illustrated embodiment, the mobile frame 40 comprises a wheeled frame 40, in particular, a road-transportable trailer 40. However, according to alternative embodiments, the mobile frame 40 may comprise other road-transportable wheeled vehicles (e.g., truck). According to alternative embodiments, the mobile frame 40 may comprise a rail-transportable vehicle (e.g., railroad car). According to alternative embodiments of the CNG mobile storage system 20, the mobile frame 40 may comprise a water-transportable mobile frame (e.g., a barge, boat, etc.). According to various alternative embodiments, the mobile frame 40 may comprise a skid that is transportable via a flat-bed truck or trailer.

According to various embodiments, the vessel 30 may comprise one or more CNG storage tanks. For example, the vessel 30 comprises a plurality of CNG storage modules that are loaded onto and removably (or permanently) supported by a 40 foot trailer 40 being pulled by a tractor. Each module may comprise a plurality of CNG storage tanks.

According to various embodiments, the vessel 30 contains CNG at a pressure that is (1) at least 200, 1000, 1200, 1500, 2000, 2500, 3000, 3200, 3500, and/or 4000 psig (2) less than 5000, 4500, 4000, 3800, 3700, 3600, 3000, 2500, 2000, and/or 1500 psig and/or (3) within any range within such upper and lower values (e.g., between 200 and 2000 psig, between 1000 and 3600 psig, between 200 and 5000 psig). According to various embodiment, CNG is transferred into the vessel 30 at a location that is geographically separated from the compressor 410 by at least 0.1, 0.5, 1, 2, 3, 4, 5, 7.5, 10, 15, 20, 30, 40, 50, 75, 100, 150, 200, 20, 300, 100, and/or 200 miles. The CNG mobile storage system 20 is then transported (e.g., via road, rail, water) to the site of the well 20.

According to various embodiments, the CNG mobile storage system 20 complies with regulations for road transportation of CNG (e.g., DOT 49 CFR, ASME B31.3, and/or API RP 200/505).

According to various embodiments, the CNG mobile storage system 20 may comprise any of the mobile transport systems disclosed in W02014/031999 A2 (filed Aug. 23, 2013, titled "Virtual Gaseous Fuel Pipeline") and/or U.S. Provisional Patent Application No. 62/279,388 (filed Jan. 15, 2016, titled "Compressed Natural Gas Artificial Gas Lift"), the entirety of each of which are incorporated herein by reference. Additionally and/or alternatively, the CNG mobile storage system 20 may incorporate any of the CNG mobile storage system features and/or components described in such applications.

Mobile CNG Unloader 100

As shown in FIG. 1, the CNG unloader 100 connects the vessel 30 to the compressor 410 to control the flow of CNG from the vessel 30 to the compressor 410.

Figure 2:
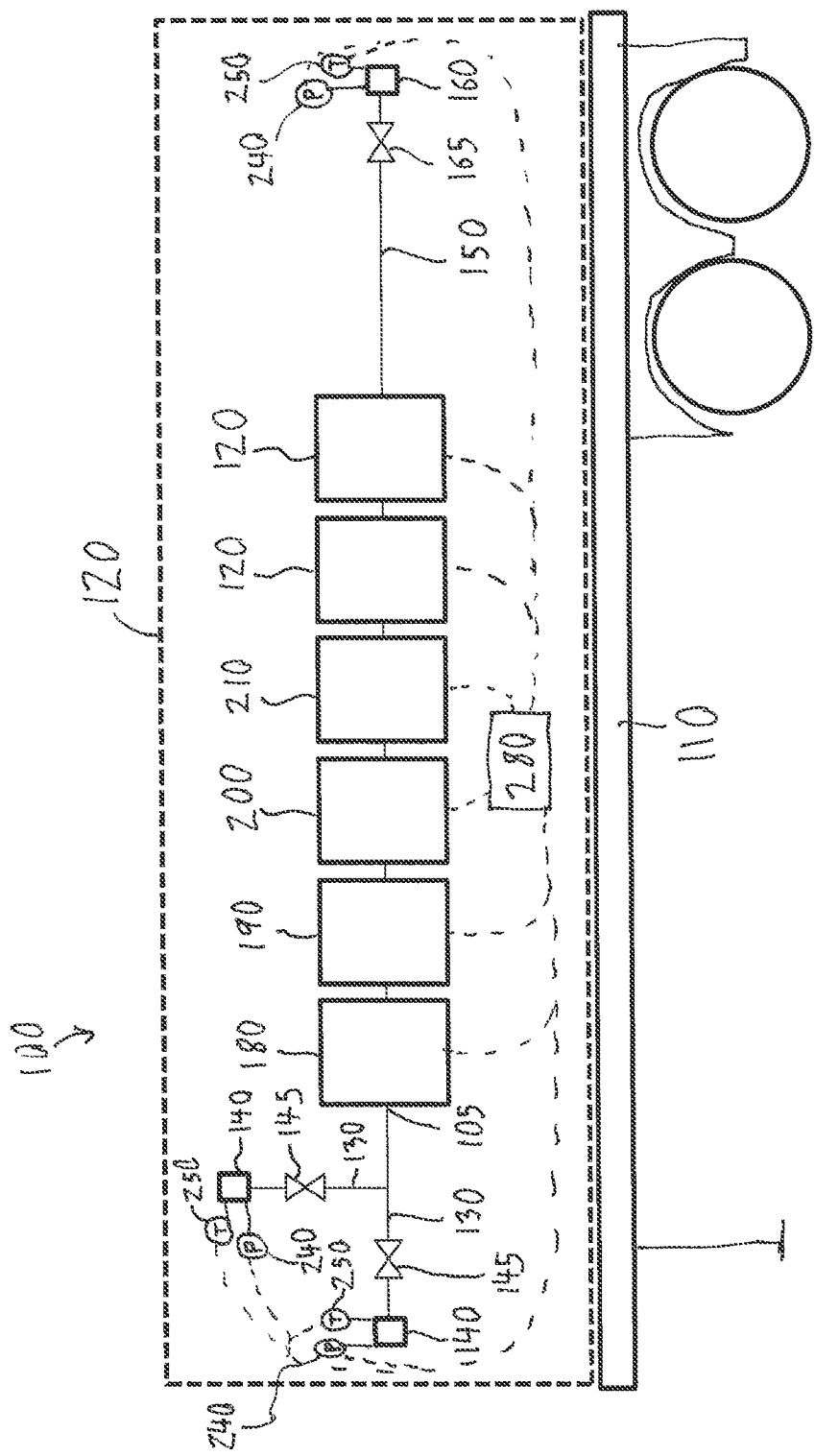
FIG. 2 is a diagrammatic side view of a mobile CNG unloader according to various embodiments of the test system illustrated in FIG. 1.
Figure 4:
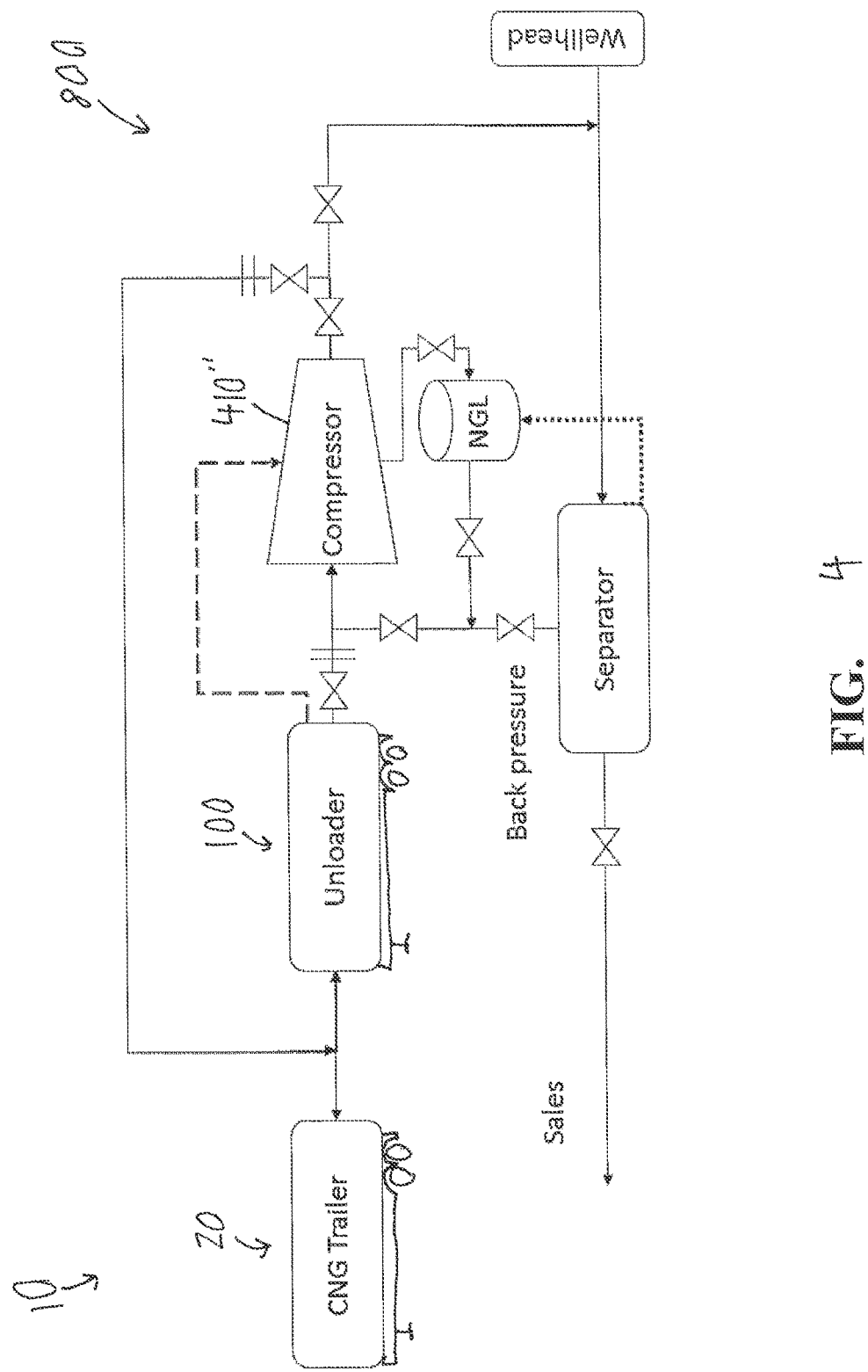
FIG. 4 is a diagrammatic view of the compressor test system of FIG. 1 being used with a vapor recovery compressor of a well.

As shown in FIG. 2, the unloader 100 comprises a mobile frame 110 and unloader equipment 120. The mobile frame 110 may be similar to or identical to any of the mobile frames 40 discussed above with respect to the CNG mobile storage system 20 (e.g., a trailer, skid, rail car, barge, boat etc.). As illustrated in FIG. 4, the mobile frame 110 may comprise a road-transportable, wheeled trailer that is 20 feet long or less according to various embodiments. According to various embodiments, the CNG Unloader 100 complies with ASME B31.3 and/or API RP 200/505.

According to various embodiments, the unloader's mobile frame 110 is eliminated altogether, and the unloader equipment 120 is supported by (removably or permanently) the CNG mobile storage system's mobile frame 40 so that the vessel 30 and unloader equipment 120 are transportable together as a unit to and from the site of the compressor 410.

As shown in FIG. 2, the unloader equipment 120 comprises a multi-branched inlet conduit 130 (e.g., flexible hoses, rigid pipes, etc.) that interconnects an inlet 105 of the unloader 100 with two inlet connectors 140. As shown in FIG. 1, the inlet connectors 140 detachably connect an inlet 105 of the unloader equipment 120 (1) to the vessel 30 to receive CNG from the vessel 30, and (2) to an outlet 490 of the compressor 410 to receive CNG from the compressor 410. Valves 145 are disposed in the conduit 130. The unloader equipment 120 comprises an outlet conduit 150 (e.g., a flexible hose, a series of rigid pipes, etc.) and outlet connector 160 configured to connect the unloader equipment 120 to the inlet 440 of the compressor 410. A valve 165 is disposed in the conduit 150.

CNG flowing from the inlet conduit 130 to the outlet conduit 150 passes sequentially through various components of the unloader equipment 120.

According to various embodiments, the unloader equipment 120 includes a pressure regulator 180 that controls and reduces the pressure of CNG received from the vessel 30 so as to provide CNG to the compressor 410 at a desired pressure, which is typically lower than a pressure within the vessel 30 and an outlet pressure of the CNG compressed by the compressor 410. According to various embodiments, the pressure regulator 180 is manually adjustable by a user so that the user can select the pressure at which CNG is provided to the inlet 440 of the compressor 410.

According to alternative embodiments, the pressure regulator 180 is automated (e.g., via mechanical and/or electronic automation). For example, the pressure regulator may be computer controlled (e.g., via the below-discussed computer 280).

According to various embodiments, the unloader equipment 120 includes a CNG meter 190 to meter the amount (e.g., in terms of mass and/or volume (e.g., scf)) of CNG that is transferred from the vessel 30 to the compressor 410. The meter 190 may comprise any suitable meter (e.g., an orifice plate meter).

According to various embodiments, the unloader equipment 120 includes flow rate control equipment 200 (e.g., a manual or automatic flow rate control valve, a manual or automated choke valve, a manual or automatic adjustable orifice plate). According to various embodiments, the flow control equipment 200 is manually adjustable by a user so that the user can select the flow rate (e.g., in terms of mass and/or volumetric rate) at which CNG is provided from the vessel 30 to the compressor 410. According to alternative embodiments, the flow rate control equipment 200 is automatically controlled (e.g., by the below-discussed computer 280).

The flow control equipment 200 may be configured to stop CNG flow entirely. However, additional shut-off valve(s) may also be positioned anywhere along the flow path between the vessel 30 and the compressor 410 (e.g., the valves 145, 165). All of the valves 145, 165 may be opened to operate the test system 10.

According to various embodiments, the unloader equipment 120 includes a heater 210. According to various embodiments, the heater 210 is powered by natural gas that is supplied from the vessel 30. The heater 210 may include a user-selectable temperature input, and may automatically heat the CNG so as to deliver the CNG to the inlet 440 of the compressor 410 at a desired temperature or within a desired temperature range. The heater 210 may be controlled by the computer 280 and use a feedback loop from a temperature sensor (e.g., sensor 250) to ensure that the delivered CNG is within the desired temperature range. According to various embodiments, the heater 210 is a thermostat-controlled heater that ensures that the CNG delivered to the inlet 440 of the compressor has a temperature of (1) at least −20, −10, 0, 10, 20, 30, 40, 50, and/or 60 degrees F., (2) less than 150, 140, 130, 120, 110, 100, 90, 80, and/or 70 degrees F., and/or (3) between any two such upper and lower values (e.g., between −20 and 150 degrees F., between 30 and 100 degrees F.). The heater 210 may be useful in situations where a large pressure drop from the high-pressure vessel 30 or compressor outlet 490 would otherwise cause excessive Joule-Thompson cooling of the CNG being supplied to the inlet 440 of the compressor 410. For example, the heater 210 may prevent or discourage overly cold conditions along the flow path of the CNG (e.g., temperatures below the rated temperatures of the valves or conduits along the flow path).

As shown in FIG. 1, the heater 210 may include a heat exchanger 215 that transfers heat from the compressed gas output by the compressor 410 to the gas in the passageways 150, 570 leading to the compressor's inlet 440 or engine 565. The heat exchanger has the dual benefit of heating the gas that was cooled by the unloading process, and cooling the gas that was heated by the compressing process.

Additionally and/or alternatively, the unloader equipment 120 may comprise additional and/or alternative components 120, for example, any of the unloader components or features described in W02014/031999 A2 and/or U.S. Provisional Patent Application No. 62/279,388.

According to various embodiments, as shown in FIG. 2, the unloader equipment 120 includes a variety of pressure sensors 240 and temperature sensors 250 that measure CNG conditions at various points in the system 10 (e.g., the CNG being received by the unloader 100, the CNG being delivered to the compressor 410). In FIG. 2, the sensors 240, 250 are illustrated as being disposed at the connectors 140, 160. However, the sensors 240, 250 may alternatively be disposed at any other suitable point along the flow path of the CNG between and among the vessel, unloader 10, and compressor 410.

According to various embodiments, the unloader equipment 120 includes a computer 280 (e.g., a PC, laptop, tablet, programmable controller, or other computer) that is operatively connected to the sensors 240, 250, other equipment 120 (e.g., pressure regulator 180, CNG meter 190, flow control equipment 200, heater 210), and/or other sensors in the system 10 (e.g., flow rate and/or pressure sensors of the compressor 410) to track and record the operational characteristics of the system 10 during use. The computer 280 may connect to a data transmission system (e.g., internet, WIFI, SCADA, LAN, WAN, Ethernet, digital or analog connection, phone connection, cellular network) to provide (1) a live feed of such operational characteristics of the system 10 and/or (2) provide historical data for such operational characteristics for past operation of the system 10.

According to various embodiments, the computer 280 may allow the user to enter the desired pressure and flow rate of gas being provided to the inlet of the compressor 410. Additionally and/or alternatively, the computer 280 and unloader 100 may operate to ensure that an outlet pressure of CNG at the outlet 490 of the compressor 410 remains above a predetermined value to ensure that the compressor 410 operates at a desired load. The unloader 100 and computer 280 (or a user) may also control the valve 145 to control a pressure within the conduit 130 that is connected to the outlet 490 of the compressor 410.

While the individual components of unloader equipment 180, 190, 200, 210, 120, 530 are illustrated in FIG. 2 in a particular sequential order, the components 120 may alternatively be arranged in any other order without deviating from the scope of the invention.

While a variety of exemplary unloader equipment 120 is illustrated, any component(s) of the unloader 120 may be eliminated or altered without deviating from the scope of the invention.

Compressor Site 400

As shown in FIG. 1, the test system 10 is connected to the compressor 410 at the compressor site 400. In the illustrated compressor site 400, the compressor 410 comprises a pipeline booster station compressor 400 disposed in a natural gas transmission pipeline 420 (e.g., natural gas commercial supply pipeline). An inlet conduit 430 connects the low-pressure inlet 440 of the compressor 410 to (1) an upstream side of the CNG pipeline 420 so that the upstream side of the pipeline 420 feeds the compressor 410 with CNG, and (2) a connector 450 that detachably connects to the connector 165 to operatively connect an outlet of the unloader 100 to the inlet 440 of the compressor 410. A valve 470 may be disposed in the upstream side of the pipeline 420 and may be turned off during use of the system 10 to disconnect the compressor 410 from the upstream pipeline 420 and feed the compressor 410 only with natural gas received from the vessel 30 or recirculated from the high-pressure outlet 490 of the compressor 410.

An outlet conduit 500 connects the compressor's high-pressure outlet 490 to (1) a downstream side of the natural gas pipeline 420 so that the compressor 410 feeds natural gas to the downstream pipeline 420 and downstream users/consumers of natural gas, and (2) a connector 520 that detachably connects to one of the connectors 140 so that the compressor 410 feeds compressed gas back to the inlet 105 of the unloader 100.

A valve 540 may be disposed in the downstream side of the pipeline 420 and may be turned off during use of the system 10 to isolate the compressor 410 from the downstream pipeline 420 so that all compressed gas output by the compressor 410 feeds back to the inlet 105 of the unloader. Additionally and/or alternatively, the valve 540 may be partially opened during use of the system 10 to help ensure that the compressor's outlet pressure (e.g., the pressure within the conduit 500) remains within a desired range for the desired load on the compressor 410. The valve 540 may be manually controlled by a user, may be pressure-controlled (e.g., by opening when the upstream pressure in the conduit 500 exceeds a predetermined minimum, for example in the form of a pressure relief valve 540), and/or may be controlled by the computer 280.

According to various embodiments, the compressor 410 is a gas powered compressor (e.g., comprising an internal combustion engine 565 (e.g., spark plug ignited internal combustion engine, diesel engine) that drives a compressor portion of the compressor 410), and the emissions tests are directed toward emissions of the compressor's engine 565. As shown in FIG. 1, the unloader 100 may feed fuel gas from the vessel 30 to the compressor's engine 565 via a fuel gas supply conduit 570 to power the engine 565 of the compressor 410 during the testing. According to various embodiments, the CNG supplied by the vessel 30 is a lean CNG that results in low compressor emissions when the compressor's engine 565 burns the CNG from the vessel 30 during emissions testing. According to various embodiments, the vessel 30 supplies fuel gas to the compressor 410 only during startup of the compressor 410, after which point the compressor 410 is fed with fuel gas as a result of its operation (e.g., within a vapor recovery system as illustrated in FIG. 4). According to various other embodiments, the vessel 30 is the sole source of fuel gas for the compressor 410 throughout the testing.

Use Of The Test System 10

To use the system 10, the system 10 (including the CNG mobile storage system 20 and compressed gas unloader 100) is transported to the geographic site 400 of the compressor 410 and connected to the compressor 410 as shown in FIG. 1. The valves 145, 165 are opened. The valves 470, 540 are optionally closed or opened (depending on whether the user desires to run the test while pipeline 420 gas continues to flow through the compressor 410). The valve 540 may be controlled throughout the testing so as to only open when an outlet pressure of the compressor 410 (e.g., at the outlet 490 and/or in the conduit 500) exceeds a predetermined minimum pressure for a desired load factor of the compressor 410 during testing.

According to various embodiments, the valve 470 may be closed and the valve 540 may be opened during the test so that a supply of CNG continues to be delivered to the downstream side of the pipeline 420 without interrupting CNG service to the downstream user(s). In such an embodiment, the CNG being supplied to the downstream users may come almost entirely from the vessel 30 during the testing (subject to residual native gas in the conduits when the test started).

The unloader 100 is then operated to transfer CNG from the vessel 30 to the compressor 410. First, CNG is transferred from the vessel 30 to the inlet of the unloader 100. The unloader 100 reduces a pressure of the received gas (and optionally otherwise conditions the gas (e.g., by heating it or cooling it), and transfers the reduced pressure gas from the unloader 100 to the inlet 440 of the compressor 410. The unloader 100 controls a pressure of the reduced pressure CNG being transferred to the inlet of the compressor 410 so that the pressure of the reduced pressure gas at the inlet 440 of the compressor 410 remains within a predetermined pressure range. According to various embodiments, the predetermined pressure range may comprise a 5, 10, 20, 30, 40, 50, 60, 70, 80, 90, 100, 150, 200, 250, 300, 350, 400, 450 and/or 500 psi range. According to various embodiments, that psi range may be centered at a psig pressure of (1) at least 5, 10, 20, 30, 40, 50, 60, 70, 80, 90, 100, 150, 200, 250, 300, 350, 400, 450, 500, 600, 700, 800, 900, 1000, 1100, 1200, 1300, 1400, 1500, 1750, 2000, 2250, 2500, 2750, 3000, 3250, and/or 3500 psig, (2) less than or equal to 6000, 5500, 5250, 5000, 4750, 4500, 4250, 4000, 3750, 3500, 3250, 3000, 2750, 2500, 2250, 2000, 1900, 1800, 1700, 1600, 1500, 1400, 1300, 1200, 1100, 1000, 900, 800, 700, 600, 500, 450, 400, 350, 300, 250, and/or 200 psig, and/or (3) within any range bounded by any two such numbers (e.g., between 5 and 6000 psig, between 500 and 6000 psig, between 900 and 5000 psig, between 1000 and 3600 psig, between 1000 and 2000 psig, about 1500 psig, between 200 and 1000 psig, between 300 and 750 psig, between 300 and 600 psig, between 400 and 500 psig, and/or about 450 psig). The compressor 410 recompresses the reduced pressure gas received from the unloader 100 and transfers at least a portion of the recompressed gas to the inlet 105 of the unloader 100. As a result, at least a portion of the compressed gas received by the unloader 100 from the vessel 30 is recirculated between the unloader 100 and the compressor 410.

According to various embodiments, an outlet pressure of the compressor 410 (i.e., at the compress's outlet 490 and in the conduit 500) is kept within a predetermined range during the testing by selectively opening and/or closing (either completely or partially) the valves 145 and/or 540 and/or by controlling the unloader 100 to keep an inlet pressure of the unloader 100 (and thereby the outlet pressure of the compressor 410) within the desired predetermined range. As a result, according to various embodiments, during the recirculating and testing, an outlet pressure of the compressor 411 (i.e., at the compress's outlet 490 and in the conduit 500) is of (1) at least 5, 10, 20, 30, 40, 50, 60, 70, 80, 90, 100, 150, 200, 250, 300, 350, 400, 450, 500, 600, 700, 800, 900, 1000, 1100, 1200, 1300, 1400, 1500, 1750, 2000, 2250, 2500, 2750, 3000, 3250, and/or 3500 psig, (2) less than or equal to 6000, 5500, 5250, 5000, 4750, 4500, 4250, 4000, 3750, 3500, 3250, 3000, 2750, 2500, 2250, 2000, 1900, 1800, 1700, 1600, 1500, 1400, 1300, 1200, 1100, 1000, 900, 800, 700, 600, 500, 450, 400, 350, 300, 250, and/or 200 psig, and/or (3) within any range bounded by any two such numbers (e.g., between 5 and 6000 psig, between 500 and 6000 psig, between 900 and 5000 psig, between 1000 and 3600 psig, between 1000 and 2000 psig, about 1500 psig, between 200 and 1000 psig, between 300 and 750 psig, between 300 and 600 psig, between 400 and 500 psig, and/or about 450 psig).

According to various embodiments, the unloader 100 controls the flowrate of CNG through the compressor 410 during the recirculation and testing. The valves 145, 540, 470 may also be selectively controlled (e.g., by the user, by the computer 280, as pressure-controlled valves (e.g., pressure relief valves). As a result of one or more of these features, the flowrate of CNG through the compressor 410 during the testing and recirculating is (1) at least 20, 30, 40, 50, 60, 70, 80, 90, 100, 125, 150, 175, 200, 225, 250, 275, 300, 350, 400, 450, 500, 550, 600, 650, 700, 750, 800, 900, 1000, 1250, 1500, 2000, 2500, 3000, 3500, 4000, 4500, and/or 5000 mscfd (thousand standard cubic feet per day), (2) less than or equal to 5000, 4500, 4000, 3500, 3000, 2500, 2000, 1500, 1250, 1000, 900, 800, 750, 700, 650, 600, 550, 500, 450, 400, 350, 300, 275, 250, 200, 175, 150, 140, 130, 120, 110, 100, 90, and/or 80 mscfd, and/or (3) within any range bounded by any two such numbers (e.g., between 20 and 5000 msdfd, between 75 and 150 mscfd, between 300 and 600 mscfd, between 500 and 5000 mcfd).

Figure 3:
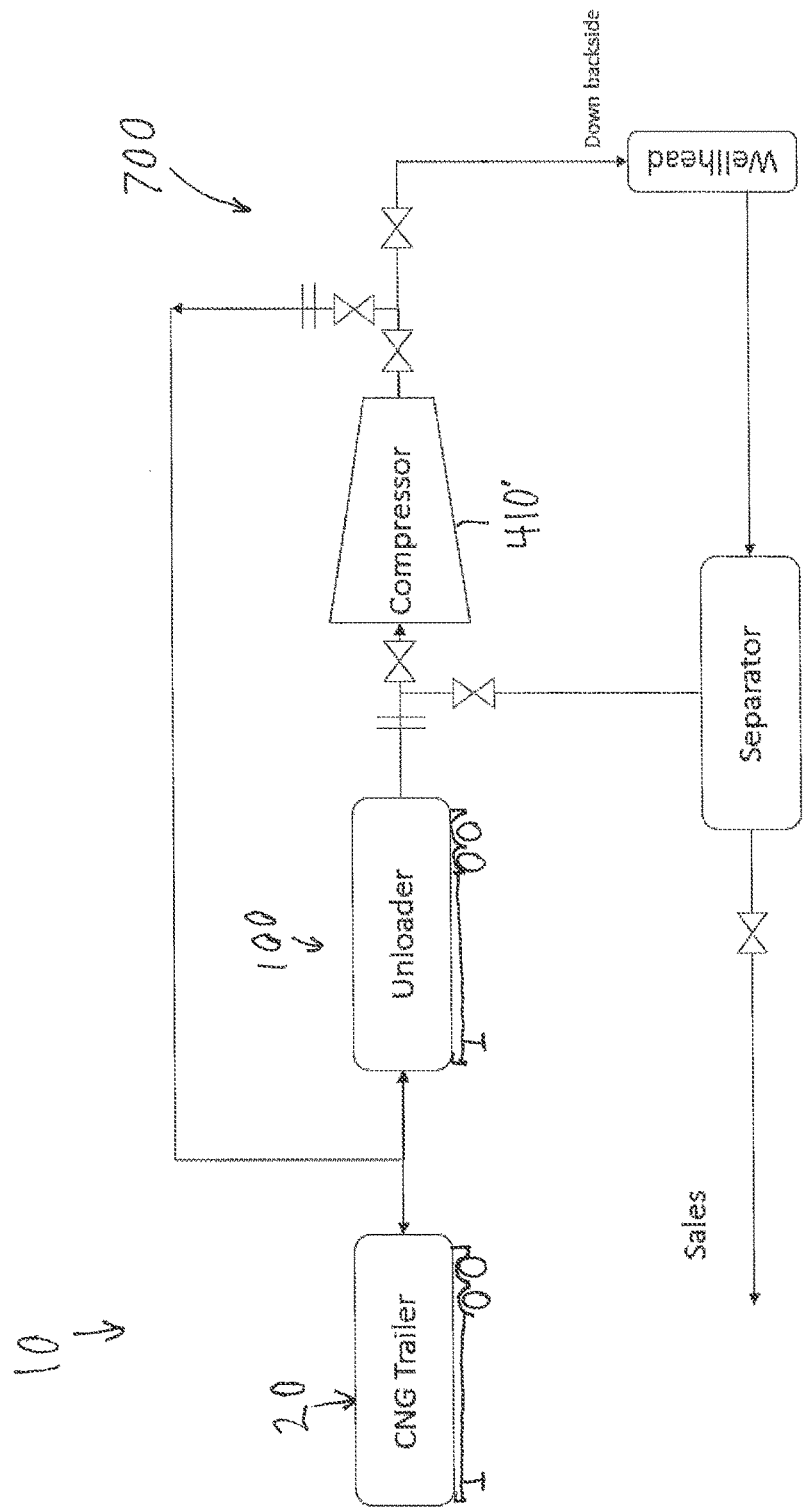
FIG. 3 is a diagrammatic view of the compressor test system of FIG. 1 being used with a compressor of a gas lift well.

The desired flowrates, compressor inlet pressures, and compressor outlet pressures used during the recirculation and testing are determined by the particular compressor 410 being tested and the desired load (e.g., as a function of rated load). For example, in a compressor 410 disposed in a natural gas commercial transmission line according to one or more embodiments, the flow rate is 500-5000 mscfd and the outlet pressure is about 1500 psig. In a compressor 410 used for gas lift in a well (e.g., as illustrated in FIGS. 3-4) according to one or more embodiments, the flow rate is 300-600 mscfd and the outlet pressure is about 1500 psig. In a compressor 410 used for gas lift in a well equipped with vapor recovery (e.g., as illustrated in FIG. 4) according to one or more embodiments, the flow rate is 75-150 mscfd and the outlet pressure is about 450 psig.

During the recirculating, the vessel 30 may act as a buffer vessel 30 to accept excess CNG provided from the outlet 490 of the compressor 410 (e.g., when the output of the compressor 410 exceeds the supply requirements or flow capacity of the downstream pipeline 420 or flow capacity of the unloader 100). Additionally and/or alternatively, the vessel 30 may continuously or intermittently provide makeup CNG to unloader 100 to ensure that the gas being supplied to the inlet of the compressor 410 is sufficient in pressure and flowrate. Such makeup gas may be used if the downstream end of the pipeline 420 is being supplied with CNG throughout the compressor 410 testing (e.g., to avoid supply interruptions to the downstream side of the pipeline 420). During the recirculating, sufficient CNG may be transferred from the vessel 30 to the unloader 100 that the compressor 410 continuously operates at at least a predetermined portion of a rating of the compressor 410. According to various embodiments, the predetermined portion may be 50, 60, 70, 80, 90, 95, and/or 100% of a rated load of the compressor 410.

If the valves 470 and 540 are closed during the recirculation and testing, the setup may form a closed loop between the unloader 100 and compressor 410, with the vessel 30 acting as a buffer/expansion vessel 30. As used herein, the setup is considered closed loop even though CNG from the vessel 30 may also be used/consumed to power the gas-powered compressor 410. Alternatively the system 10 may be setup as an open loop in which (1) additional CNG is provided from a source in addition to the vessel 30 (e.g., the upstream side of the pipeline 420, a wellhead (see FIG. 3), an NGL tank (see FIG. 4)), and/or (2) CNG compressed by the compressor 410 is split downstream such that a portion of the CNG is recirculated, while another portion is delivered downstream (e.g., to the downstream end of the pipeline 420, to a wellhead (see FIGS. 3, 4)).

According to various embodiments, mobile transport systems 20 and multiple vessels 30 may be connected in parallel with each other to the unloader 100, for example, via additional branches of the conduit 130 and additional parallel connectors 140. Such vessels 30 may be used simultaneously to provide a larger supply of available natural gas and/or buffer capacity. Additionally and/or alternatively, separate vessels 30 may be sequentially connected to the unloader 100 over the course of the testing to account for depletion of vessels 30. In such embodiments, a fresh vessel 30 may be connected to the unloader 100 before the prior vessel 30 is depleted and detached from the unloader 100 so as to ensure a continuous supply of natural gas to the unloader 100 and compressor 410 during the testing.

During the recirculation, emissions test equipment 600 is used to emissions test the compressor 410. The emissions testing may comprise regulatory emissions testing (e.g., U.S. EPA quad J testing).

According to various embodiments, during the recirculating and testing, the compressor 410 may be powered by CNG (or other compressed fuel gas) received from the compressed gas storage vessel 30. According to various embodiments, natural gas supplied by the vessel 30 is burned by the engine 565 of the compressor 410 at a rate of (1) at least 2, 5, 10, 15, 20, 25, 30, 40, 50, 60, 70, 80, 90, and/or 100 mscfd, (2) less than 200, 150, 100, 90, 80, 70, 60, 50, 40, 30, 25, 20, 15, and/or 10 mscfd, and/or (3) in any range between any two such upper and lower values (e.g., between 2 and 100 mscfd, between 5 and 50 mscfd, between 10-30 mscfd, and/or about 20 mscfd).

According to various embodiments, the system 10 reduces the testing frequencies (e.g., for a regulatory requirement that requires less frequent testing for tests closer to the compressor's rated load), and/or improves the chances of passing the test by reducing emissions and increasing the acceptable emissions tolerance window (e.g., for a regulatory requirement that widens the emissions tolerance window for tests closer to the compressor's rated load).

Other Compressors 410

While the compressor 410 illustrated in FIG. 1 is a pipeline booster station compressor 410, the system 10 may alternatively and/or additionally be used to emissions test any other compressor 410. For example, as illustrated in FIG. 3, the system 10 may be used to test a gas lift compressor 410' that is part of a gas lift well 700. As illustrated in FIG. 4, the system 10 may be used to test a vapor recovery compressor 410" that is part of a well 800.

In the illustrated embodiments, the operating fluid being provided by the vessel 30 and recirculated between the unloader 100 and compressor 410 comprises CNG. However, according to alternative embodiments, the operating fluid may comprise any other type of suitable compressible operating fluid (e.g., other fuel gases (e.g., propane), non-fuel gas).

The foregoing illustrated embodiments are provided to illustrate the structural and functional principles of various embodiments and are not intended to be limiting. To the contrary, the principles of one or more of these embodiments are intended to encompass any and all changes, alterations and/or substitutions thereof (e.g., an alterations within the spirit and scope of the following claims).

What is claimed is:

1. A method for testing a compressor, the method comprising:
    transferring compressed gas from a storage vessel of a mobile compressed gas storage system to an inlet of a compressed gas unloader;
    recirculating at least a portion of the compressed gas received by the unloader between the unloader and a compressor, said recirculating comprising:
        reducing, via the unloader, a pressure of compressed gas received at the inlet of the unloader,
        transferring the reduced pressure gas from the unloader to an inlet of the compressor,
        recompressing, via the compressor, the reduced pressure gas received from the unloader, and
        transferring at least a portion of the recompressed gas back to the inlet of the unloader; and
    during the recompressing, conducting emissions testing on the compressor.

2. The method of claim 1, wherein the compressed gas comprises a compressed fuel gas.

3. The method of claim 2, wherein:
    the compressor includes a gas-powered engine for driving a compressor portion of the compressor, and
    the method further comprises, during the recirculating, powering the engine with the compressed fuel gas received from the compressed gas storage vessel.

4. The method of claim 1, wherein:
    the compressor includes a gas-powered engine for driving a compressor portion of the compressor, and
    said conducting emissions testing on the compressor comprises conducting emissions testing on the engine.

5. The method of claim 1, wherein the emissions testing comprises regulatory emissions testing that is required by a regulatory authority for the compressor.

6. The method of claim 5, wherein the regulatory emissions testing comprises U.S. EPA Quad J testing.

7. The method of claim 1, wherein, during the recirculating, the compressed gas storage vessel acts as a buffer vessel to accept excess compressed gas from the compressor.

8. The method of claim 1, wherein, during the recirculating, the compressed gas storage vessel provide makeup compressed gas to unloader.

9. The method of claim 1, further comprising, during the recirculating, transferring sufficient compressed gas from the compressed gas storage vessel to the compressed gas unloader that the recompressing occurs at at least a predetermined portion of a rating of the compressor.

10. The method of claim 9, wherein the predetermined portion is 90% of a rating of the compressor.

11. The method of claim 1, wherein the compressor is one of: a pipeline booster station compressor, a vapor recovery compressor of a well, and a gas lift compressor of a gas lift well.

12. The method of claim 1, further comprising, before the recirculating, transporting the compressed gas storage vessel and the unloader to a geographical site where the compressor is located.

13. The method of claim 1, wherein, during the recirculating, the unloader controls a pressure of the reduced pressure gas being transferred to the inlet of the compressor so that the pressure of the reduced pressure gas at the inlet of the compressor remains within a predetermined pressure range.

14. The method of claim 1, wherein, during the recirculating, the unloader controls a temperature of the reduced pressure gas being transferred to the inlet of the compressor so that the temperature of the reduced pressure gas at the inlet of the compressor remains within a predetermined temperature range.

15. The method of claim 1, wherein, during the recirculating, the unloader controls a pressure of the gas being received by the unloader's inlet from the compressor's outlet so that an outlet pressure of the compressor remains above a predetermined value.

16. The method of claim 1, further comprising:
before conducting the emissions testing, disconnecting the compressor from a downstream gas line that the compressor's outlet feeds during the compressor's routine operation; and
after conducting the emissions testing, reconnecting the compressor to the downstream gas line.

17. The method of claim 1, further comprising:
before conducting the emissions testing, disconnecting the compressor from an upstream gas supply line that feeds the compressor during the compressor's routine operation; and
after conducting the emissions testing, reconnecting the compressor to the upstream gas supply line.

18. A system for emissions testing a compressor, the system comprising:
the compressor, the compressor having an inlet and an outlet;
a mobile compressed gas storage system including a compressed gas vessel supported by a wheeled frame, the compressed gas vessel containing compressed gas at a supply pressure; and
an unloader having an inlet and an outlet, the inlet of the unloader being fluidly connected to the vessel and the outlet of the compressor, the outlet of the unloader being fluidly connected to the inlet of the compressor,
wherein the system is configured to recirculate compressed gas through the unloader and compressor during emissions testing of the compressor.

* * * * *